United States Patent
Hansson et al.

(10) Patent No.: US 11,366,073 B2
(45) Date of Patent: Jun. 21, 2022

(54) DENSITY ANALYSIS OF GEOLOGICAL SAMPLE

(71) Applicant: OREXPLORE AB, Kista (SE)

(72) Inventors: Alexander Hansson, Kista (SE); Mikael Bergqvist, Kista (SE)

(73) Assignee: OREXPLORE AB, Kista (SE)

( * ) Notice: Subject to any disclaimer, the term of this patent is extended or adjusted under 35 U.S.C. 154(b) by 0 days.

(21) Appl. No.: 17/264,236

(22) PCT Filed: Jul. 18, 2019

(86) PCT No.: PCT/SE2019/050703
§ 371 (c)(1),
(2) Date: Jan. 28, 2021

(87) PCT Pub. No.: WO2020/027714
PCT Pub. Date: Feb. 6, 2020

(65) Prior Publication Data
US 2021/0302337 A1    Sep. 30, 2021

(30) Foreign Application Priority Data

Aug. 3, 2018 (SE) .................................. 1850954-7

(51) Int. Cl.
*G01N 23/00* (2006.01)
*G01N 23/223* (2006.01)
(Continued)

(52) U.S. Cl.
CPC .............. *G01N 23/223* (2013.01); *G01N 9/36* (2013.01); *G01N 23/2206* (2013.01); *G01N 2223/076* (2013.01); *G01N 2223/616* (2013.01)

(58) Field of Classification Search
None
See application file for complete search history.

(56) References Cited

U.S. PATENT DOCUMENTS

| 5,063,509 | A | 11/1991 | Coles et al. | |
|---|---|---|---|---|
| 10,247,682 | B2 * | 4/2019 | Schlecht | G01N 23/046 |

(Continued)

FOREIGN PATENT DOCUMENTS

| EP | 1933170 A1 | 6/2008 |
|---|---|---|
| WO | 2013/058672 A1 | 4/2013 |

OTHER PUBLICATIONS

International Search Report and Written Opinion dated Dec. 2, 2019, issued in International patent application No. PCT/SE2019/050703, filed Jul. 18, 2019, 13 pages.

*Primary Examiner* — Hoon K Song
(74) *Attorney, Agent, or Firm* — Christensen O'Connor Johnson Kindness PLLC

(57) ABSTRACT

An apparatus (100) for analysing a sample (101) comprising a drill core sample or drill cuttings is provided. The apparatus comprises an X-ray geological structure data unit configured to scan the sample to obtain a data set indicating a volume of the sample, a fluorescence detector (109) configured to measure fluorescent radiation emanating from the sample (101) when irradiated by the X-ray beam, and a weighing unit (105) configured to weigh the sample. The apparatus further comprises a processing unit (104) configured to calculate a density of the sample (101) based on the data set obtained by the X-ray geological structure data unit, the fluorescent radiation measured by the fluorescence detectors, and the weight provided by the weighing unit.

7 Claims, 4 Drawing Sheets

(51) Int. Cl.
*G01N 9/36* (2006.01)
*G01N 23/2206* (2018.01)

(56) References Cited

U.S. PATENT DOCUMENTS

2014/0072095 A1* 3/2014 Feser .................. G01N 23/223
378/4
2014/0376685 A1* 12/2014 Koroteev ............... G01N 33/24
378/4

* cited by examiner

DENSITY ANALYSIS OF GEOLOGICAL SAMPLE

TECHNICAL FIELD

The present inventive concept generally relates to the field of analysis of drill core samples and/or drill cuttings. In particular, the present disclosure relates to a method and device for analysing a sample during X-ray transmission measurements.

BACKGROUND

In mineral exploration, gathering accurate information about known or potential ore deposits may be important for geologists in order to assess whether to begin, continue or abandon mining operation within a certain area. Using specialized drills, samples of rock may be withdrawn from an orebody in the form of drill cores and/or drill cuttings, and analysed for e.g. mineral contents, stratigraphic data and/or other geological information that may be of importance to the geologist.

To analyse the drill core samples and/or drill cuttings, various flavours of measurements may be performed in order to gather data about the samples before attempting to analyse and identify the constituents of for example the rock from where the samples were withdrawn. These analyses may be performed at a laboratory, to which the samples may be sent and analysed by means of e.g. X-ray diffraction and fluorescence measurements.

However, sending the samples to laboratories is known to be a time consuming process associated with long lead times. Thus, in light of the above there is a need for a cost efficient and faster way of analysing geological samples.

SUMMARY

An objective of the present inventive concept is therefore to at least partially fulfil the above requirements. This and other objectives are achieved by means of an apparatus for analysing a sample as defined in the independent claim. Further embodiments of the present disclosure are provided in the dependent claims.

According to an aspect of the present disclosure there is provided an apparatus for analysing a sample comprising a drill core sample or drill cuttings. The apparatus may include an X-ray geological structure data unit configured to scan the sample to obtain a data set indicating a volume of the sample, a processing unit configured to calculate the volume of the sample based on the obtained data set and a weighing unit configured to weigh the sample. The processing unit may be configured to calculate a density of the sample based on the weight and the calculated volume of the sample.

The X-ray geological structure data unit may include an X-ray source for generating an X-ray beam irradiating the sample, an X-ray transmission detector for detecting the X-ray beam passing through the sample, and a sample holder for holding the sample. The apparatus may further include a rotating means for rotating at least one of the X-ray source, the X-ray transmission detector, and the sample holder during irradiation of the sample. With this arrangement, the sample may be rotated relative the X-ray source and detector to allow for the attenuation of the X-ray beam to be determined at different positions within the sample. These measurements may in some examples be tomography measurements.

The apparatus may further comprise a fluorescence detector configured to measure fluorescent radiation emanating from the sample when irradiated by the X-ray beam. Thus, the fluorescence detector serves the purpose of capturing fluorescent rays or radiation emanating from the sample. By using fluorescence measurements, the concentrations of chemical elements in the sample may be determined by measuring the fluorescent (secondary) rays emitted from the sample when excited by a primary ray source. By knowledge of what elements would generate what fluorescent rays, the material composition of the sample may be studied and used in combination with the volume and density measurements to provide an improved characterisation of the overall composition of the sample. Thus, by combining several techniques, such as both X-ray transmission analysis, density analysis and fluorescence analysis, a more complete knowledge about the site or deposit being examined may be deduced.

By scanning each sample with an X-ray geological structure data unit, internal structures, such as voids, cavities, and porosities, may be taken into consideration when calculating the volume. This is advantageous over prior art technologies based on e.g. fluid displacement, which tend to neglect internal voids and other factors affecting the actual volume of the material forming the sample. Thus, by employing an X-ray based technology for calculating the volume of the sample, the density may be more accurately determined.

Further, by integrating a weighing unit in the apparatus, the apparatus is capable of retrieving all information necessary for determining the density. Advantageously, the apparatus can be placed in the vicinity of the test site at from which the samples are withdrawn, thereby allowing for a relatively fast and convenient on-site analysis without any need for additional or external measurements or analyses of the sample.

The present inventive concept is based on the insight that by determining the density of the sample by means of the volumetric and/or attenuation data obtained by the X-ray measurements and the weight information from the weighing unit, a more accurate and thorough analysis of the contents of the sample can be achieved. The density information may be a valuable complement to the information pertaining to the structural composition determined by the differences in X-ray attenuation and to the compositional distribution of elements determined by e.g. fluorescence measurements.

In some embodiments, the information obtained by the X-ray measurements, such as for instance X-ray transmission measurements and fluorescence measurements, can be used to theoretically estimate a density, or density distribution, of the sample. The estimation can for example be based on an estimated volume of the sample, and/or attenuation information indicating a density distribution (which can be assumed to correlate to the attenuation of X-ray radiation). Further, the fluorescence measurement may indicate a material composition of the sample, for example in terms of elements present at least at the surfaces, or near the surfaces, of the sample. The material composition can be used to estimate possible minerals that can be present in the sample, and this information can then be combined with the X-ray attenuation information to retrieve a possible density of the sample. The possible density that is calculated in this way may also be referred to as a theoretical density. The theoretical density may be compared with a density calculated based on the actual weight of the sample and a volume of the sample. The volume may for example be retrieved from the X-ray transmission measurements. By calculating the density in two different ways, both the theoretically based on X-ray and fluorescence measurements and the experimental based on the weight, the theoretical calculation may be adjusted and/or calibrated in order to provide an even better estimation of the sample density. Further, the difference measurement techniques, i.e., the X-ray transmission measurements, the fluorescence measurements and the weighting, may complement each other in an advantageous manner. The X-ray transmission measurements may reveal information about invisible interior structures and voids of the sample, whereas the fluorescence measurements may give a more precise information about actual elements and potential minerals in the sample. Both these measurements may give information about a distribution within or at least along the sample, i.e., they may be performed to retrieve information about characteristics at different positions of the sample. This differs from the weighting, which may give accurate information about the total weight of the sample, but no information about how the weight is distributed within the sample. By combining two of the measurements, or all three of them, the density measurements may be improved and more accurate.

The term "X-ray geological structure data unit" may hence refer to a device utilising X-ray irradiation so as to retrieve information of the interior of the sample. This may for example be achieved by means of X-ray transmission, wherein differences in X-ray attenuation that arise from differences in e.g. atomic number, density and composition within the sample can be used to gather information of the internal composition and structure of the sample. This may for example be used in a tomography process, in which one or more two-dimensional slices revealing the interior of the sample may be obtained.

The obtained data set may be used to calculate the volume of the sample, which may be understood as the volume occupied by the material forming the sample. The volumetric data may for example be obtained by combining several tomography slices mentioned above, resulting in a volume measure that may take interior void, pores and cavities into consideration.

According to an embodiment, the X-ray geological structure data unit, or the X-ray tomography unit, may be configured to irradiate the sample at different axial position. Further, the processing unit may be configured to calculate the volume at different axial positions of the sample. In other words, variations in composition of the sample, leading to variations in attenuation, may be determined along the axial direction. This allows for a possibility of understanding a density distribution along the axial direction of the sample based on X-ray measurements, which thus may be used as a complement to the weight information and/or the fluorescence information so as to more accurately estimate the density distribution of the sample.

According to an embodiment the sample holder may include a confining structure that extends in the axial direction and is adapted to, during measurement, at least partially enclose the sample and to restrict movement of the sample in a direction that intersects the axial direction. The confining structure may include at least one region facing away from the axial direction and allowing exciting radiation impinging on, and fluorescent radiation emanating from, the sample during measurement to pass therethrough.

By restricting the sample from moving in a direction that intersects the axial direction, the sample may be held fixed such that it does not move in an unwanted direction or in an unwanted way during measurement. This may result in an improved resolution and a more accurate result, especially for X-ray transmission measurements but also for fluorescence measurements.

While the sample is held fixed, in the above sense, radiation coming from e.g. a ray source may pass through the at least one region that faces away from the axial direction and impinge on the sample, with little or no attenuation caused by the sample holder itself. Likewise, radiation emanating from the sample during e.g. fluorescence measurements may pass through the at least one region that faces away from the axial direction and reach e.g. a ray detector also with little or no attenuation caused by the sample holder itself. This may result in an improved resolution and a more accurate result, especially for fluorescence measurements but also for X-ray transmission measurements.

A sample holder in accordance with the present disclosure thereby achieves the synergetic effect of both fixing the sample during measurement, and at the same time allowing for radiation to impinge on, or emanate from, the sample with little or no attenuation due to the sample holder itself.

According to an embodiment the apparatus may be further configured such that a plane of extension of the at least one region of the sample holder at least momentarily aligns with a plane defined by the positions of the X-ray source, the fluorescence detector and the at least one region of the sample holder during rotation of at least one of the X-ray source, the fluorescence detector and the sample holder. By doing so, the time window available for measuring through the at least one region may be further extended.

In the context of the present disclosure, the axial direction of the confining structure is defined as the axis A along which the confining structure extends. For example, if the confining structure is assumed (for illustrative purposes only) to be a cylinder of a length (L) and a diameter (D), where L>D, then the axial direction of the confining structure would be along the length of the cylinder. It is, of course, envisaged herein that the confining structure may have a shape other than that of a cylinder, but it may be assumed that the axial direction of the confining structure would generally be understood as the direction along which the confining structure has its main extension of length.

Herein, a region is defined as a region of the confining structure where the attenuation (or scattering) of radiation is less or absent compared to a part of the confining structure that surrounds the region. A region may for example be a hole in the confining structure, or a region of the confining structure with a reduced but finite thickness. A region may also be a region of the confining structure having a different material than a part of the confining structure that surrounds the region. Herein, the term region may be used interchangeably with one or more of the terms window or aperture, with regards to radiation, even though it may have a finite thickness. If X-ray radiation is used, the region may for example be transparent to or have little attenuation of X-rays while being opaque to or having high attenuation of e.g. visible light.

It will be appreciated that the confining structure may be formed of two or more different materials or structural elements. In one example, the confining structure may comprise a first material providing structural robustness or form stability, and a second material allowing the exciting radiation and/or fluorescent radiation to pass through the structure.

According to an embodiment the processing unit my further be configured to determine a content of the sample by measuring the fluorescent radiation detected along the axial direction. This is advantageous since this provides the possibility to determine a position of where the content is located in the sample.

According to another aspect of the present inventive concept, a method for analysing a sample comprising a drill core sample or drill cuttings is provided. The method may include scanning the sample to obtain a data set indicating a volume of the sample, calculating a volume of the sample based on the obtained data set, weighing the sample and calculating a density of the sample based on the weight and the calculated volume of the sample.

This aspect may generally present the same or corresponding advantages as the former aspect.

As used herein, rays may for example be X-rays, ultraviolet (UV) rays or infrared (IR) rays, and the corresponding measurements may for example be X-ray transmission measurements, X-ray fluorescence (XRF) measurements and/or UV fluorescence measurements. Likewise, a ray source may be for example an X-ray source, and a ray detector may for example be an X-ray detector or a UV or IR detector. By using X-rays, radiation having enough energy to penetrate deeper into and/or all the way through the sample may be possible. This may allow e.g. for tomographic measurements, and/or for fluorescence measurements of rays emanating from deeper within the sample than its outermost surface.

It is also envisaged that rays belonging to other parts of the electromagnetic spectrum may be used, if suitable, and that also different types of rays (such as e.g. UV and IR rays) may be used in combination.

The term "geological structure data" used in this context of the application may hereby also be referred to as "tomography".

The present disclosure relates to all possible combinations of features recited in the claims and mentioned herein, including the ones listed above as well as other features which will be described in what follows with reference to different embodiments. Any embodiment described herein may be combinable with other embodiments also described herein, and the present disclosure relates to all such combinations.

Further objects and advantages of the various embodiments of the present disclosure will be described below by means of exemplifying embodiments.

BRIEF DESCRIPTION OF THE DRAWINGS

The above, as well as additional objects, features, advantages and applications of the inventive sample holder, will be better understood through the following illustrative and non-limiting detailed description of embodiments. Reference is made to the appended drawings, in which.

Figure 1:
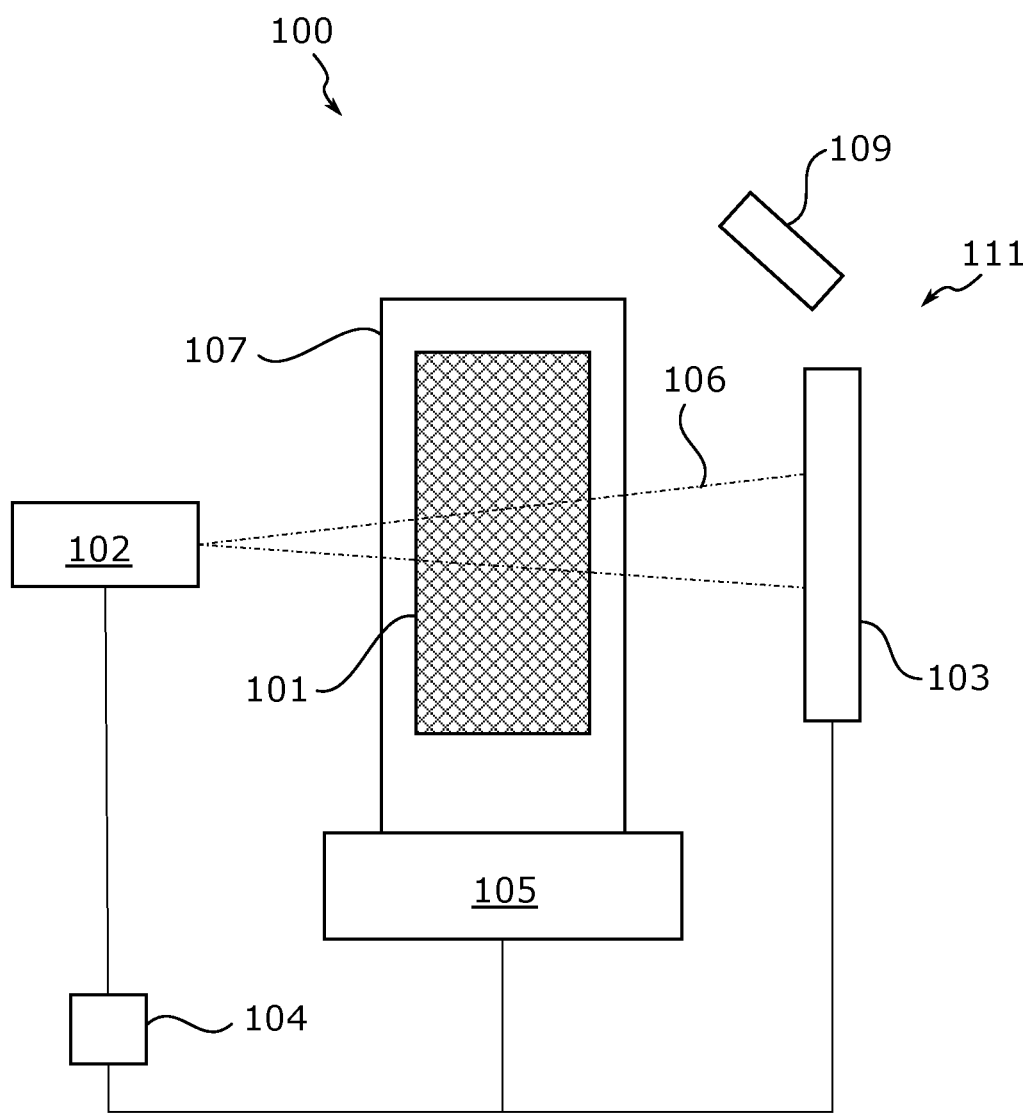
FIG. 1 illustrates the apparatus for measurement according to one or more embodiments of the present disclosure.

In the drawings, like reference numerals will be used for like elements unless stated otherwise. Unless explicitly stated to the contrary, the drawings show only such elements that are necessary to illustrate the example embodiments, while other elements, in the interest of clarity, may be omitted or merely suggested. As illustrated in the figures, the sizes of elements and regions may be exaggerated for illustrative purposes and, thus, are provided to illustrate the general structures of the embodiments.

DETAILED DESCRIPTION

Exemplifying embodiments will now be described more fully hereinafter with reference to the accompanying drawings. The drawings show currently preferred embodiments, but the invention may, however, be embodied in many different forms and should not be construed as limited to the embodiments set forth herein; rather, these embodiments are provided for thoroughness and completeness, and fully convey the scope of the present disclosure to the skilled person.

With reference to FIG. 1, an apparatus for analysing a sample including a drill core sample or drill cuttings will be described in more detail. Although the illustrated examples described in what follows all relate to measurements involving X-rays, it is, as described earlier, also envisaged that other rays (such as UV rays and IR radiation) and suitable sources and/or detectors may be used, at least for the non X-ray measurements.

FIG. 1 illustrates an apparatus 100 for analysing a sample 101. This apparatus may include an X-ray geological structure data unit, a weighing unit 105 and a processing unit 104 for determining a density of the sample based on data from the X-ray geological structure data unit and the weighing unit 105.

The X-ray geological structure data unit, which for example may be a tomography unit, may be configured to scan the sample 101 to obtain a data set indicating a volume of the sample. The volume may not only be the volume occupied by the outer periphery of the sample (e.g. corresponding to a fluid displacement volume), but to the actual volume occupied by the material forming the sample. In other words, the volume may take into account porous structures, void, cracks and the like.

Thus, the X-ray geological structure data unit may include an X-ray source 102 for generating an X-ray beam 106, an X-ray transmission detector 103 for detecting the X-ray beam 106 and a sample holder 107 for holding the sample. During operation, the X-ray source 102, the detector 103 and the sample 101 may be arranged such that the X-ray beam 106 passes through the sample 101 and the attenuation of the beam, caused by the material of the sample 101, detected by the detector 103.

The processing unit 104 may be configured to calculate the volume of the sample based on the data set obtained from the detector signal. The processing unit may in some examples be structurally integrated with the apparatus, provided as a standalone unit or arranged at another geographical location. In the latter case, the processing unit may be communicatively connected to the apparatus by means of a wired or wireless data connection link.

The weighing unit 105 may be arranged to at least partly carry the weight or load of the sample 101, thereby gathering data indicating the mass of the sample 101. The weighing unit may for example be implemented by use of a load cell using a strain gauge that is placed under the sample and such that it deflects upon load. Other examples of a weighing unit may include a force meter, or newtonmetre, which is a spring-based force meter utilising Hooke's law to indicate the mass of the sample 101. The weighing unit may be configured to measure the weight before the X-ray measurements commences, during the X-ray measurement or after they are finished.

The output from the weighing unit may then be transmitted to the processing unit 104 for calculation of the density of the sample 101. In case X-ray attenuation data is available at different axial positions of the sample 101, these may be used to estimate a density distribution along the axial direction. Thus, the average density of the entire sample may be determined as the ratio between total weight (or mass) divided by total volume, and then redistributed along the axial direction based on the differences in attenuation along the sample.

The apparatus may further comprise a fluorescence detector 109 for gathering more detailed information about the composition of the sample 101. The fluorescence measurements may be performed at various positions of the sample, such as along different axial positions so as to further complement the axial density distribution estimations.

Moreover, the apparatus may comprise rotating means for rotating at least one of the X-ray source 102, the X-ray detectors 103 and 109 and the sample holder 107 during irradiation of the sample so as to enable tomography measurements. It is also envisaged that there may be several detectors used, such as e.g. several X-ray transmission detectors, and other detectors such as e.g. fluorescent detectors. During rotation, radiation from the X-ray source 102 may impinge on a sample at different locations during measurement, and fluorescent radiation emanating from the different locations of the sample may be received by the fluorescence detector 109 and transmitted radiation emanating from the sample may be received by the X-ray detector 103. This may allow for a broader study of e.g. the concentration of chemical elements in the sample, as measurements at different locations of the sample may be obtained. This information can be used to together with the X-ray transmission measurements calculate a theoretical density of the sample.

Figure 2:
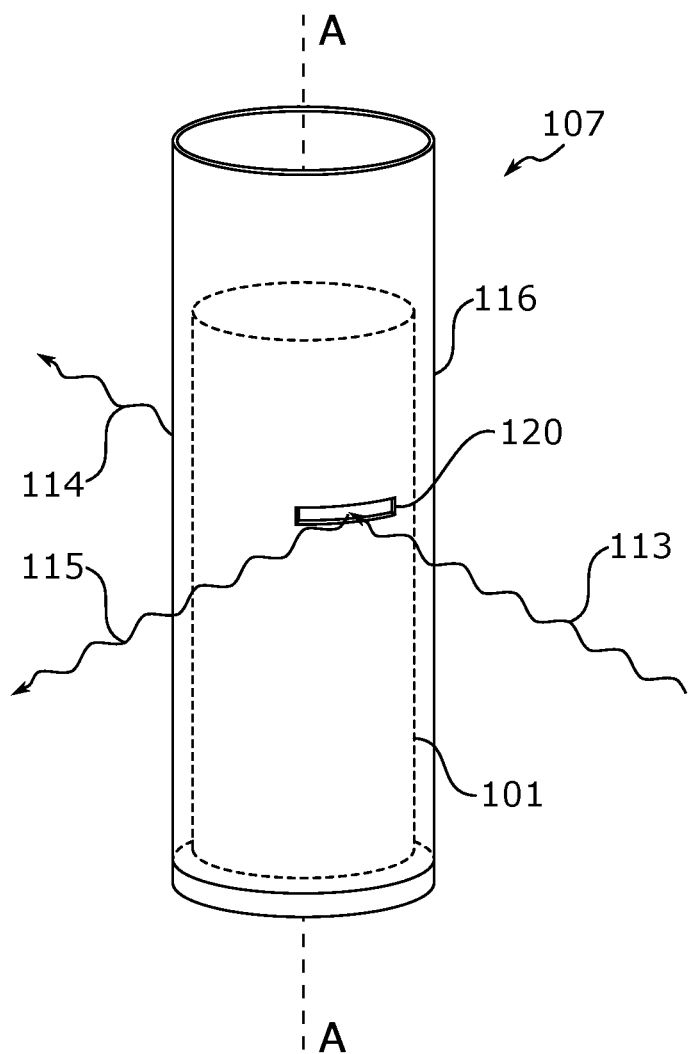
FIG. 2 illustrates a sample holder according to one or more embodiments of the present disclosure.
Figure 3:
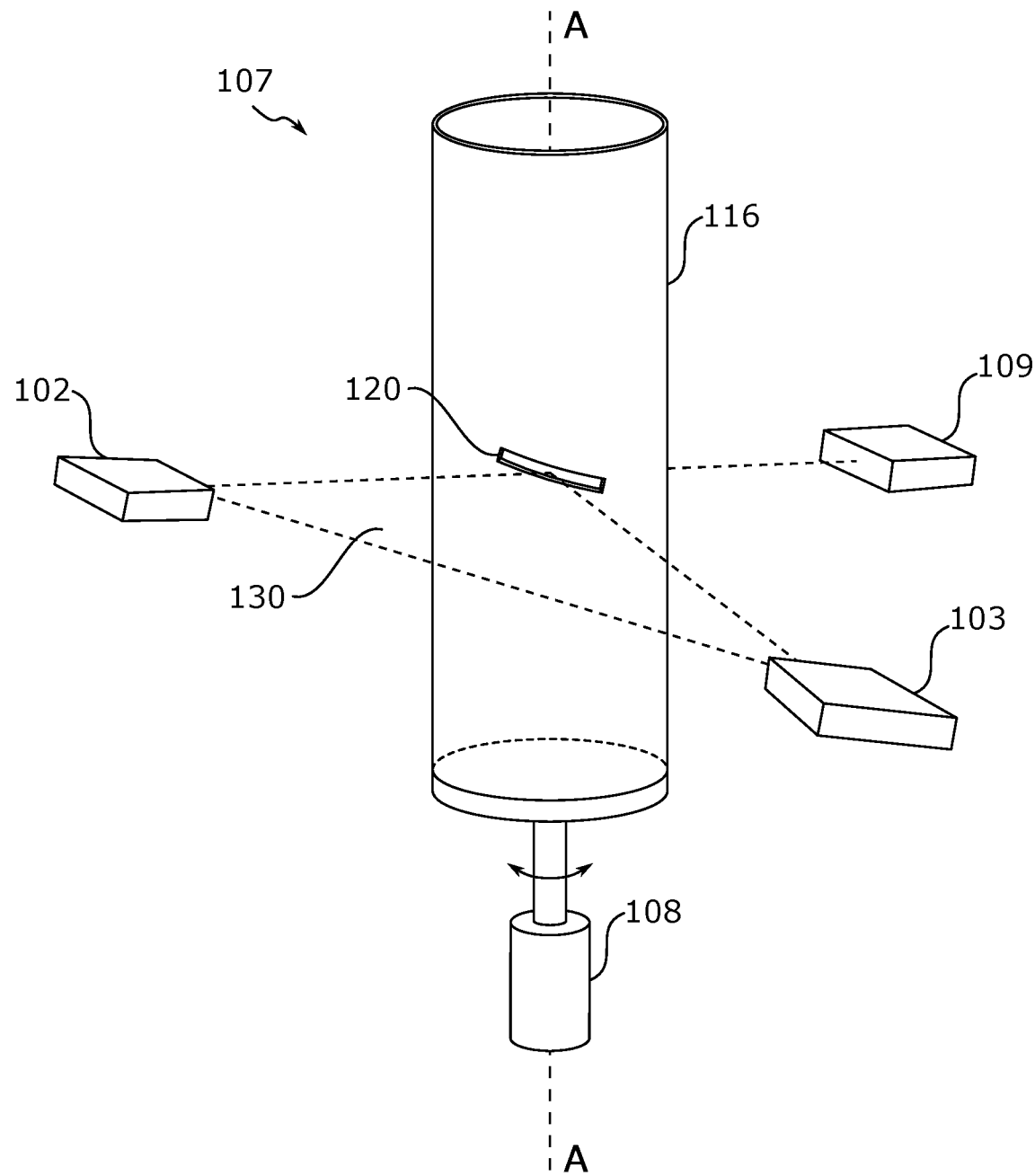
FIG. 3 illustrates a sample holder according to one or more embodiments of the present disclosure.

The rotating means may include a motor arranged to rotate the sample holder 107 around the axial direction A (see FIGS. 2 and 3). The motor may for example be a DC motor, a synchronous motor or e.g. a stepper motor. It is envisaged that rotating means may also be provided for rotating the X-ray source 102 and/or one or both of the X-ray detectors 103 or 109.

The X-ray source 102 may for example be an X-ray tube, a radioactive isotope, or any other suitable source. The X-ray source 102 may for example generate X-rays based on triboluminescence.

The X-ray fluorescence detector 109 may for example be a scintillation detector, a semiconductor detector, a quantum dot detector or any other suitable detector.

If using radiation with other wavelengths (e.g. UV and IR radiation), a radiation source may be e.g. a UV lamp, led or laser, and a detector may be e.g. a semiconductor UV or IR photo diode or similar.

With reference to FIG. 2, the sample holder 107 used in FIG. 1 is shown. The sample holder 107 may include a confining structure 116 that has an axial direction A. This confining structure 116 may be formed as a hollow cylinder. It is, however, envisaged that the confining structure 116 may have other forms, as for example a square, rectangular, oval, hexagonal or e.g. some other n-sided polygonal hollow tube or pipe. The confining structure 116 encloses the sample 101 and restricts it from moving in a direction that intersects the axial direction A. During measurement, exciting radiation 113 coming from e.g. an X-ray source and which impinges on the sample may pass through the region 120 (which faces away from the axial direction A) of the confining structure 116 with no or little attenuation, emanate from the sample 101 as transmitted radiation 114, and continue towards for example an X-ray transmission detector. Likewise, fluorescent radiation 115 which emanates from the sample 101 during measurement may also pass through the region 120 with no or little attenuation, and continue towards for example an X-ray fluorescence detector.

The bottom of the sample holder 107 may be sealed with a base, which may be of the same or of a different material as that of the confining structure 116. The base may be a separate piece, or form part of the confining structure 116. The weighing unit may be located under the base but may also be located above holding the sample holder 107. However, the position may depend on the kind of weighing unit that is used.

The output from the weighing unit may be transmitted to the processing unit 104 and used for verifying, adjusting or calibrating the theoretically calculated density.

In some embodiments, the material of which the confining structure 110 is made has a majority of atoms having an atomic number of 9 or less, such that the interaction of the atoms with the X-ray radiation may be reduced. As an example, the material may be e.g. carbon or materials based on polymers.

FIG. 3 illustrates an apparatus which includes a sample holder 107 as described herein, at least one X-ray source 102, at least one X-ray fluorescence detector 109 and at least one X-ray transmission detector 103. Although used for different purposes, it is envisaged that the detectors 103 and 109 may also be of a same type. As illustrated in FIG. 3, the positions of the region 120, the X-ray source 102 and the X-ray detector 103 defines a plane 130. By aligning the region 120 such that its plane of extension aligns with the plane 130, the process of measuring may be improved. If, for example, the sample 101 is being rotated by a rotating means, aligning the region 120 such that its plane of extension aligns with the plane 130 may allow for radiation to impinging on or emanate from the sample through the region 120 during a larger time interval during measurement. In the present, illustrative example the rotating means may be integrated with a weighing unit for determining the mass of the sample. Thus, the weighing unit may be arranged to carry the weight of the sample holder and sample, and to deliver a signal from which the mass of the sample can be derived.

The X-ray source 102 and the X-ray (transmission) detector 103 may be constructed such that they rotate along with each other, or the X-ray source 102 and the X-ray detector 103 may be aligned individually, using e.g. separate or joint means of rotation (such as e.g. motors).

Figure 4:
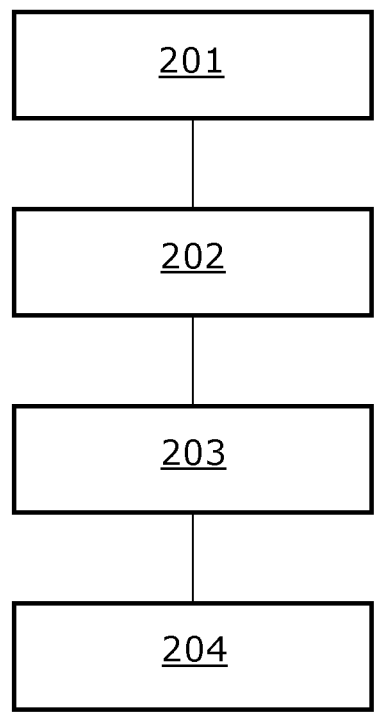
FIG. 4 is a block diagram illustrating the method according to one or more embodiments of the present disclosure.

With reference to FIG. 4, a block diagram illustrating the method for analysing a sample is shown. This method uses the apparatus as described in relation to FIG. 1.

The method comprises scanning the sample to obtain a data set indicating a volume of the sample 201, calculating a volume of the sample 101 based on the obtained data set 202, weighing the sample 203 and calculating a density of the sample 101 based on the weight and the calculated volume of the sample 204.

The person skilled in the art realizes that the present disclosure is by no means limited to the embodiments described above. On the contrary, many modifications and variations are possible within the scope of the appended claims.

Although features and elements are described above in particular combinations, each feature or element may be used alone without the other features and elements or in various combinations with or without other features and elements.

Additionally, variations to the disclosed embodiments can be understood and effected by the skilled person in practicing the claimed invention, from a study of the drawings, the disclosure, and the appended claims. The mere fact that certain features are recited in mutually different dependent claims does not indicate that a combination of these features cannot be used to advantage.

The invention claimed is:

1. An apparatus for analysing a sample comprising a drill core sample or drill cuttings, said apparatus comprising:
   an X-ray geological structure data unit configured to scan the sample to obtain a data set indicating a volume of the sample, the X-ray geological structure data unit comprising an X-ray source for generating an X-ray beam irradiating the sample, and an X-ray transmission detector for detecting the X-ray beam passing through the sample;
   a fluorescence detector configured to measure fluorescent radiation emanating from the sample when irradiated by the X-ray beam to obtain a fluorescence data set;
   a processing unit configured to calculate the volume of the sample based on the obtained data set; and
   a weighing unit configured to weigh the sample;
   wherein the processing unit is further configured to calculate a density of the sample based on the weight and the calculated volume of the sample, to determine a content of the sample based on the fluorescence data set, and to characterize the composition of the sample based on the calculated density and the content of the sample.

2. The apparatus according to claim 1, wherein the X-ray geological structure data unit further comprises a sample holder for holding the sample; wherein
   the apparatus further comprises a rotating means for rotating at least one of the X-ray source, the X-ray transmission detector and the sample holder during irradiation of the sample; and
   the processing unit is configured to calculate a volume of the sample based on attenuation of the X-ray beam as it passes through the sample.

3. The apparatus according to claim 2, wherein X-ray geological structure data unit is configured to irradiate the sample at different axial positions, and wherein the processing unit is further configured to calculate the volume of the sample at different axial positions.

4. The apparatus according to claim 2, wherein the sample holder comprises a confining structure extending in the axial direction and being adapted to, during measurement, at least partially enclose the sample and to restrict movement of the sample in a direction intersecting the axial direction, said confining structure comprising at least one region facing away from the axial direction and allowing exciting radiation impinging on, and fluorescent radiation emanating from, the sample during measurement to pass therethrough.

5. The apparatus according to claim 4, further configured such that a plane of extension of the least one region of the sample holder at least momentarily aligns with a plane defined by the positions of the X-ray source, the fluorescence detector and the at least one region of the sample holder during rotation of at least one of the X-ray source, the fluorescence detector and the sample holder.

6. The apparatus according to claim 1, wherein the processing unit is further configured to determine a content of the sample by measuring the fluorescent radiation detected along said axial direction.

7. A method for analysing a sample comprising a drill core sample or drill cuttings, said method comprising:
   generating, via an X-ray source, an X-ray beam irradiating the sample;
   scanning the sample with the X-ray beam to obtain a data set indicating a volume of the sample;
   measuring fluorescent radiation emanating from the sample when irradiated by the X-ray beam to obtain a fluorescence data set;
   calculating, via a processing unit, a volume of the sample based on the obtained data set;
   weighing the sample;
   calculating, via the processing unit, a density of the sample based on the weight and the calculated volume of the sample;
   determining, via the processing unit, a content of the sample based on the fluorescence data set; and
   characterizing, via the processing unit, the composition of the sample based on the calculated density and the content of the sample.

* * * * *